United States Patent [19]

Hsieh

[11] Patent Number: 5,403,929
[45] Date of Patent: Apr. 4, 1995

[54] PROCESS FOR PREPARING ALKALI SALTS OF CEPHALOSPORIN C

[75] Inventor: Chun-Lung Hsieh, Hsinchu, Taiwan

[73] Assignee: Industrial Technology Research Institute, Taiwan, Prov. of China

[21] Appl. No.: 127,244

[22] Filed: Sep. 27, 1993

[51] Int. Cl.$^6$ .......................................... C07D 501/28
[52] U.S. Cl. .................................... 540/230; 540/228
[58] Field of Search ................................ 540/228, 230

[56] References Cited

U.S. PATENT DOCUMENTS 3,661,901  5/1972  Bickel et al. .................... 540/230

Primary Examiner—Nicholas Rizzo
Attorney, Agent, or Firm—Darby & Darby

[57] ABSTRACT

Zinc salts of Cephalosporin C are dissolved in a solution of halides of univalent metals at a temperature of 0°–25° C. and the pH is adjusted to 1–2 prior to being ion exchanged with a sodium form cation-exchange resin packed in a column and being eluted with a water miscible solvent. The column can be further eluted with a solution of halides of univalent metals.

13 Claims, No Drawings

PROCESS FOR PREPARING ALKALI SALTS OF CEPHALOSPORIN C

BACKGROUND OF THE INVENTION

The present invention relates to a process for preparing alkali salts of cephalosporin C.

Cephalosporin C based antibiotics have been extensively used in inhibiting most Gram positive cocci bacteria and most Gram negative bacilli bacteria, and are particularly effective for patients who are sensitive to penicillin antibiotics.

A variey of cephalosporin C based antibiotics are synthesized from its intermediate, 7-aminocephalosporanic acid (briefly referred to as 7-ACA) by replacing the amino group at the 7-position with different substituents. The intermediate, 7-ACA, is synthesized from the sodium salt of cephalosporin C by the enzymatic action of D-amino acid oxidase and glutaryl amidase.

Aqueous solutions of cephalosporin C are unstable at a pH value less than 2 at 25° C. where they convert into their ketone and thus lose their ability to inhibit the growth of bacteria. At a pH higher than 9, they convert into desacetyl cephalosporin C which only demonstrates 20% of the biological activity of cephalosporin C.

Cephalosporin C is produced from Cephalosporium using the fermentation method. As the concentration of the cephalosporin C in the fermentation broth is very low (about 2%), a zinc ion-containing solution is usually added to precipitate the cephalosporin C and recover the zinc salts. The zinc salts are then converted into sodium salts of cephalosporin C for use.

As the solubility of the zinc salts of cephalosporin C in water is low, the conventional method for converting zinc salts into sodium salts involves mixing solid zinc salts of cephalosporin C with acid form cation-exchange resins and an appropriate amount of water. By this mixing, the aqueous solution produced by the exchange of a portion of the dissolved zinc ions of cephalosporin C with the acid form cation-exchange resins will have the lower pH value of the aqueous solution. This improves the solubility of the cephalosporin C zinc salts. According to the conventional method, the reaction of the zinc salt with cation-exchange resin reaches equilibrium when the pH value is 2.0, the concentration of the cephalosporin C is 3.5%, and the concentration of the zinc salts at the equilibrium point is about 0.2%. The solution is then filtered, and separated with acid form cation-exchange resins. The filtrate is introduced into a Na form cation-exchange resin to remove the residual zinc ions. Clearly the above conventional method is quite complicated and time-consuming.

SUMMARY OF THE INVENTION

An object of the present invention is therefore to provide a simple process for improving the yield of alkali salts of cephalosporin C.

It has been found by the inventors that cephalosporin C remains stable at a pH value of 1.0–2.0 and a temperature of 0°–25° C., and a solution of halides of univalent metals improves the solubility of zinc salts of cephalosporin C in water.

Based on the above two findings, the inventors have discovered that an improved yield of alkali salts of cephalosporin C can be obtained by a process including the following steps: a) dissolving a zinc salt of cephalosporin C in a solution of a halide of a univalent metal at a temperature of 0°–25° C.; b) adjusting the pH value of the solution obtained in step a) to 1–2.0; c) ion exchanging the solution of step b) with a sodium form cation-exchange resin; and d) eluting the ion-exchanged sodium form cation-exchange resin with a water miscible solvent.

According to one aspect of the invention, the concentration of zinc salts of cephalosporin C in water increases to 17.4% after the solid zinc salts of cephalosporin C are dissolved in a solution of a halide of a univalent metal. After ion exchanging with a sodium form cation-exchange resin and eluting with a water miscible solvent, a solution containing cephalosporin C of a relative purity of 90% is obtained. The yield is about 50%. If the ion exchanged cation-exchange resin is further eluted with the solution of a halide of a univalent metal, a solution containing cephalosporin C of the same purity is obtained. The yield is about 47% which means the total yield of the process of the invention is about 97%.

The present invention can be more fully understood by reading the subsequent detailed description and examples.

DETAILED DESCRIPTION OF THE INVENTION

According to the process of the invention, the solution of halides of univalent metals is a 0.05–0.5M solution of halogenated alkali metal. Examples of the halogenated alkali metals are sodium chloride, potassium chloride and lithium chloride. Among these, sodium chloiride and potassium chloride are preferred.

The addition of zinc salts of cephalosporin C to the above solution of halides should be carried out at a temperature from 0° C. to room temperature, and preferably at around 4° C.

The above mixed solution, before ion exchanging with sodium form cation-exchange resin, should be acidified to a pH value ranging from 1 to 2. The mixed solution is poured into a column packed with the sodium form cation-exchange resin and the zinc ions are then absorbed on the cation-exchange resin upon ion exchanging with sodium ions of the cation-exchange resin. Sodium form cation-exchange resins are commercially available, for example, SK1B (Mitsubishi Chemical Industries Limited, Japan). Note that the cation-exchange resin is preferably a resin that has been treated with acid at a tempertaure of 0°–25° C. and having a pH value of 2.0–7.0.

Eluting the ion exchanged sodium form cation-exchange resin with water miscible solvents yields the solution of alkali salts of cephalosporin C. The examples of the water miscible solvents are water, methanol, ethanol, isopropanol, acetone and the mixture thereof. A preferred solvent is a mixture of methanol and water. The mixing ratio of the mixed solvent can range from 8:2 to 2:8.

The ion exchanged cation-exchange resin, after eluting with the solvent, can be further eluted with the solution of halides of univalent metals to recover the solution of alkali salts of cephalosporin C.

The following specific examples are intended to demonstrate this invention more fully without acting as a limitation upon its scope.

EXAMPLE 1

Preparation of Potassium Chloride Solution of Cephalosporin C

Suitable amounts of solid zinc salts of cephalosporin C were respectively added to 100 ml of 0.1M, 0.2M, 0.3M, 0.4M, and 0.5M solutions of potassium chloride in water under magnetic stirring. Acids were added at a temperature of 4° C. to each solution to reduce the pH to 1.8, thereby improving the solubility of the zinc salts of cephalosporin C. Solids were removed by centrifugation. The concentrations of cephalosporin C for each solution were listed in Table 1 below.

TABLE 1

| Concentration of added potassium chloride (M) | Concentration of cephalosporin C in solution |
| --- | --- |
| 0 | 3.13 |
| 0.1 | 4.03 |
| 0.2 | 11.49 |
| 0.3 | 15.20 |
| 0.4 | 17.20 |
| 0.5 | 17.70 |

EXAMPLE 2

Preparation of Sodium Chloride Solution of Cephalosporin C

The same procedures as set forth in Example 1 were repeated, except that the potassium chloride was replaced with sodium chloride. Solutions having the concentration listed in Table 2 were obtained.

TABLE 2

| Concentration of sodium chloride added | Concentration of cephalosporin C in aqueous solution |
| --- | --- |
| 0 | 3.13 |
| 0.1 | 5.17 |
| 0.2 | 17.8 |
| 0.3 | 22.2 |
| 0.4 | 23.7 |
| 0.5 | 21.9 |

EXAMPLE 3

Preparation of Sodium Salt of Cephalosporin C 0.8 ml of 7.2% solution of zinc salts of cephalosporin C was poured into a 10×180 mm column packed with 12 g SK1B cation-exchange resin (which had been treated with 2N HCl for 30 minutes, and washed with deionized water to a pH value of 2.0 and then washed with 10% sodium chloride solution to a pH of 2.0). Thereafter, the column was eluted with a solution of methanol and water (with a mixing ratio of 8:2) at a rate of 0.4 ml/min, and 64 ml of eluate was collected. The yield was 50%. The column was further eluted with 0.3M solution of potassium chloride at a rate of 0.15 ml/min, and 105 ml of eluate was collected. The yield was 47%.

It is seen from the above examples that the process of the invention is simple in Operation and the yield of alkali salts of cephalosproin C was 97%.

What is claimed is:

1. A process for preparing alkali salts of cephalosporin C, comprising the following steps:
    a) dissolving a zinc salt of cephalosporin C in a solution of a halide of a univalent metal at a temperature of 0° to 25° C.;
    b) adjusting the pH value of the solution to 1–2.0;
    c) ion exchanging the solution of step b) with a sodium form cation-exchange resin; and
    d) eluting the ion exchange sodium form cation exchange resin with a water miscible solvent.

2. The process as claimed in claim 1, wherein the halide of a univalent metal is a halogenated alkali metal.

3. The process as claimed in claim 2, wherein the halogenated alkali metal is selected from the group consisting of sodium chloride, potassium chloride and lithium chloride.

4. The process as claimed in claim 1, wherein, in step a), the zinc salt of cephalosporin C is dissolved at a temperature of 4° C.

5. The process as claimed in claim 1, wherein the concentration of the solution of the halide of a univalent metal is between 0.05 and 1.0M.

6. The process as claimed in claim 5, wherein the concentration of the solution of the halide of a univalent metal is between 0.2 and 0.5M.

7. The process as claimed in claim 1, wherein the sodium form cation-exchanged resin has been treated at a temperature of 0°–25° C. and has a pH value of 2.0–7.0.

8. The process as claimed in claim 1, wherein the solvent is selected from the group consisting of water, methanol, ethanol, isopropanol, acetone and mixtures thereof.

9. The process as claimed in claim 1, wherein the solvent is a mixture of water and a water miscible solvent.

10. The process as claimed in claim 9, wherein the mixing ratio of water and water miscible solvent is in the range of 8:2–2:8.

11. The process as claimed in claim 1, further comprising the step of eluting the ion exchanged cation-exchange resin after step d) with a solution of a halide of a univalent metal.

12. The process as claimed in claim 11, wherein the solution of a halide of a univalent metal is a 3M sodium chloride solution.

13. The process as claimed in claim 11, wherein the solution of a halide of a univalent metal is a 3M potassium chloride solution.

* * * * *

UNITED STATES PATENT AND TRADEMARK OFFICE
CERTIFICATE OF CORRECTION

PATENT NO. : 5,403,929
DATED : April 4, 1995
INVENTOR(S) : Chun-Lung HSIEH

It is certified that error appears in the above-indentified patent and that said Letters Patent is hereby corrected as shown below:

Title page, [75] Inventor: after "Taiwan" add --Republic of China--;

[73] Assignee: change "Prov. of China" to --Republic of China--.

Signed and Sealed this

Eleventh Day of July, 1995

Attest:

BRUCE LEHMAN

Attesting Officer    Commissioner of Patents and Trademarks